United States Patent
Lalonde et al.

(10) Patent No.: US 10,098,685 B2
(45) Date of Patent: Oct. 16, 2018

(54) FEEDBACK SYSTEM FOR CRYOABLATION OF CARDIAC TISSUE

(71) Applicant: MEDTRONIC CRYOCATH LP, Toronto (CA)

(72) Inventors: Jean-Pierre Lalonde, Candiac (CA); Regina E. Groves, Dellwood, MN (US); Timothy G. Laske, Shoreview, MN (US); Paul A. Iaizzo, White Bear Lake, MN (US); John C. Bischof, Saint Paul, MN (US)

(73) Assignee: Medtronic CryoCath LP, Toronto, Ontario (CA)

( * ) Notice: Subject to any disclaimer, the term of this patent is extended or adjusted under 35 U.S.C. 154(b) by 382 days.

(21) Appl. No.: 14/192,512

(22) Filed: Feb. 27, 2014

(65) Prior Publication Data
US 2015/0119868 A1   Apr. 30, 2015

Related U.S. Application Data
(60) Provisional application No. 61/897,444, filed on Oct. 30, 2013.

(51) Int. Cl.
| A61B 18/02 | (2006.01) |
| A61B 18/14 | (2006.01) |
| A61B 18/00 | (2006.01) |

(52) U.S. Cl.
CPC ............... *A61B 18/02* (2013.01); *A61B 18/14* (2013.01); *A61B 2018/0022* (2013.01);
(Continued)

(58) Field of Classification Search
CPC ............ A61B 18/02; A61B 2018/0262; A61B 2018/0268; A61B 2018/0212; A61B 2018/00821; A61B 2018/00797
See application file for complete search history.

(56) References Cited

U.S. PATENT DOCUMENTS
| 597,945 A | 1/1898 | Bradley |
| 4,107,937 A | 8/1978 | Chmiel |
(Continued)

FOREIGN PATENT DOCUMENTS
| CA | 2724154 A1 | 11/2009 |
| CN | 103200890 A | 7/2013 |
(Continued)

OTHER PUBLICATIONS
International Search Report and Written Opinion dated Jan. 20, 2015, for corresponding International Application No. PCT/CA2014/000773, International Filing Date: Oct. 27, 2014, consisting of 8-pages.
(Continued)

*Primary Examiner* — Ronald Hupczey, Jr.
(74) *Attorney, Agent, or Firm* — Christopher & Weisberg, P.A.

(57) ABSTRACT

A method and system for providing lesion depth feedback during an ablation procedure. In particular, the method and system provide feedback data or information relating to lesion depth in myocardial tissue during a cryoablation procedure. A plurality of tissue temperature measurements may be transmitted from a plurality of thermocouples disposed on a cryotreatment element, which measurements may be used to determine a slope of change in temperature sensed by each thermocouple over time. The circulation of coolant through the treatment element may be adjusted when the slope changes. A change in slope may indicate that the cryoablation temperatures have passed through target myocardial tissue into non-target, non-myocardial tissue, which may result in collateral damage to structures near the heart.

14 Claims, 8 Drawing Sheets

(52) U.S. Cl.
CPC ............ *A61B 2018/00357* (2013.01); *A61B 2018/00577* (2013.01); *A61B 2018/00714* (2013.01); *A61B 2018/00738* (2013.01); *A61B 2018/00744* (2013.01); *A61B 2018/00797* (2013.01); *A61B 2018/00821* (2013.01); *A61B 2018/0212* (2013.01); *A61B 2018/0262* (2013.01)

(56) References Cited

U.S. PATENT DOCUMENTS

| | | | | |
|---|---|---|---|---|
| 5,433,717 | A | * | 7/1995 | Rubinsky ............... A61B 18/02 600/411 |
| 5,654,279 | A | * | 8/1997 | Rubinsky ............... A61B 18/02 128/DIG. 27 |
| 5,899,897 | A | | 5/1999 | Rabin et al. |
| 6,602,247 | B2 | * | 8/2003 | Lalonde ............ A61M 25/0029 606/21 |
| 7,341,586 | B2 | | 3/2008 | Daniel et al. |
| 7,402,161 | B2 | | 7/2008 | Zvuloni et al. |
| 7,479,139 | B2 | | 1/2009 | Cytron et al. |
| 8,012,147 | B2 | * | 9/2011 | Lafontaine ............. A61B 18/02 606/20 |
| 8,945,107 | B2 | * | 2/2015 | Buckley ................ A61B 18/02 606/21 |
| 8,961,506 | B2 | * | 2/2015 | McCarthy ........... A61B 18/082 606/20 |
| 9,066,720 | B2 | * | 6/2015 | Ballakur ............... A61B 18/10 |
| 9,314,290 | B2 | * | 4/2016 | Fourkas ................ A61B 18/02 |
| 2002/0042610 | A1 | * | 4/2002 | Sliwa, Jr. ........... A61B 17/2202 606/27 |
| 2002/0161361 | A1 | * | 10/2002 | Sherman ............ A61B 18/1206 606/34 |
| 2003/0139738 | A1 | | 7/2003 | Ali et al. |
| 2006/0015092 | A1 | | 1/2006 | Joye et al. |
| 2006/0100495 | A1 | | 5/2006 | Santoianni et al. |
| 2006/0184163 | A1 | | 8/2006 | Breen et al. |
| 2007/0049915 | A1 | * | 3/2007 | Haemmerich ..... A61B 18/1492 606/32 |
| 2008/0027420 | A1 | * | 1/2008 | Wang ................... A61B 18/02 606/21 |
| 2008/0154258 | A1 | * | 6/2008 | Chang ................ A61B 18/1482 606/41 |
| 2008/0161890 | A1 | | 7/2008 | Lafontaine |
| 2008/0312644 | A1 | * | 12/2008 | Fourkas ................ A61B 18/02 606/22 |
| 2009/0118723 | A1 | * | 5/2009 | Lalonde ................ A61B 18/02 606/21 |
| 2009/0287201 | A1 | | 11/2009 | Lalonde et al. |
| 2009/0306638 | A1 | | 12/2009 | Hillely et al. |
| 2010/0168725 | A1 | * | 7/2010 | Babkin ................. A61B 18/02 606/21 |
| 2010/0179527 | A1 | | 7/2010 | Watson et al. |
| 2011/0152855 | A1 | * | 6/2011 | Mayse ............... A61B 18/1492 606/33 |
| 2011/0301587 | A1 | * | 12/2011 | Deem ................ A61B 18/1815 606/33 |
| 2012/0089047 | A1 | * | 4/2012 | Ryba ..................... A61B 18/02 600/554 |
| 2012/0109118 | A1 | * | 5/2012 | Lalonde ................. A61N 1/403 606/21 |
| 2012/0143179 | A1 | * | 6/2012 | Avitall ............... A61B 18/1492 606/33 |
| 2012/0259322 | A1 | * | 10/2012 | Fourkas ................ A61B 18/02 606/21 |
| 2013/0110099 | A1 | | 5/2013 | Groves et al. |
| 2013/0184696 | A1 | * | 7/2013 | Fourkas ................ A61B 18/02 606/24 |
| 2013/0184700 | A1 | * | 7/2013 | Dalal ................ A61B 18/1206 606/33 |
| 2013/0190745 | A1 | * | 7/2013 | Fourkas ................ A61B 18/02 606/25 |
| 2014/0012155 | A1 | * | 1/2014 | Flaherty ................ A61B 5/015 600/549 |
| 2014/0243808 | A1 | * | 8/2014 | Molnar-Hammond ..................... A61B 18/02 606/23 |
| 2014/0276539 | A1 | * | 9/2014 | Allison ................. A61B 18/02 604/500 |
| 2014/0343543 | A1 | * | 11/2014 | Karnik .................. A61B 18/02 606/24 |
| 2015/0126985 | A1 | * | 5/2015 | Newell ................. A61B 18/02 606/21 |
| 2015/0196740 | A1 | * | 7/2015 | Mallin .................. A61B 18/02 606/21 |
| 2015/0230851 | A1 | * | 8/2015 | Lalonde ................ A61B 18/02 606/23 |

FOREIGN PATENT DOCUMENTS

| | | |
|---|---|---|
| CN | 102027427 B | 10/2013 |
| CN | 102715950 B | 10/2015 |
| EP | 1830729 A1 | 9/2007 |
| EP | 1467667 B1 | 4/2010 |
| EP | 2268190 A2 | 1/2011 |
| EP | 2632363 A1 | 9/2013 |
| WO | 2013147990 A1 | 10/2013 |

OTHER PUBLICATIONS

J.C. Bishof et al., An Analytical Study of Cryosurgery in the Lung, Journal of Biomechanical Engineering, Nov. 1992, vol. 114 /467.
Notice on the First Office Action and Search Report, dated Sep. 13, 2017, The State Intellectual Property of the People's Republic of China, corresponding application No. 201480059848.X, 5 pages.
Supplementary European Search Report, dated May 17, 2017, corresponding Application No. EP 14858556, 10 pages.

* cited by examiner

FEEDBACK SYSTEM FOR CRYOABLATION OF CARDIAC TISSUE

CROSS-REFERENCE TO RELATED APPLICATION

This application is related to and claims priority to U.S. Provisional Patent Application Ser. No. 61/897,444, filed Oct.30, 2013, entitled ACCESSORY TO ALLOW SENSING AT BALLOON INTERFACE, the entirety of which is incorporated herein by reference.

STATEMENT REGARDING FEDERALLY SPONSORED RESEARCH OR DEVELOPMENT n/a

FIELD OF THE INVENTION

The present invention relates to a method and system for providing feedback during an ablation procedure in order to monitor lesion formation in target tissue and avoidance of unintentional damage to non-target tissue.

BACKGROUND OF THE INVENTION

A cardiac arrhythmia is a condition in which the heart's normal rhythm is disrupted. Certain types of cardiac arrhythmias, including ventricular tachycardia and atrial fibrillation, may be treated by ablation (for example, radiofrequency (RF) ablation, cryoablation, ultrasound ablation, laser ablation, microwave ablation, and the like), either endocardially and/or epicardially.

The success of an ablation procedure depends largely on the quality of the lesion(s) created during the procedure. Further, in the case of pulmonary vein isolation (PVI) using a cryoablation balloon, success may depend on whether the cryoballoon has completely occluded the pulmonary vein (PV) being treated. In any ablation procedure, however, an important concern is preventing damage to non-target tissue, particularly non-cardiac tissue. For example, when performing PVI, non-target tissues such as the lungs, esophagus, vagus nerve, and phrenic nerve may be thermally affected by the treatment of the target tissue within the heart. This collateral damage may have permanent undesired effects on these non-target tissues.

There are several ways in which such non-target tissues may be monitored for the onset of thermal damage during an ablation procedure. For example, damage to the phrenic nerve may be detected by monitoring diaphragm function, and techniques such as fluoroscopy, electrocardiography and pacing, intracardiac echocardiography, and transesophageal or transthoracic ultrasound imaging may be used to directly visualize epicardial structures in an attempt to prevent collateral damage. However, these methods may involve the use of a great deal of additional complex and expensive equipment, and the procedures may be time-consuming and the results difficult to interpret.

Therefore, it is desired to provide a method and system for generating feedback during an ablation procedure in order to monitor lesion formation in target tissue and avoid unintentional damage to non-target tissue. It is further desired to provide a method and system for generating feedback that is easy to use, does not involve additional equipment, and can be used during an ablation procedure to allow for real-time monitoring.

SUMMARY OF THE INVENTION

The present invention advantageously provides a method and system for providing lesion depth feedback during an ablation procedure. In particular, the method and system may provide feedback data or information relating to lesion depth in myocardial tissue during a cryoablation procedure correlating to temperature measurements, and this feedback may indicate when cryoablation temperatures have reached non-target, non-myocardial tissue.

In one embodiment, the method may include taking a plurality of temperature measurements with one or more thermocouples, determining a slope of a change of temperature over time for each of the one or more thermocouples, and adjusting a temperature of a treatment element in contact with the myocardial tissue when the slope changes. The treatment may be a cryoballoon, which may be in fluid communication with a coolant supply reservoir. Adjusting the temperature of the treatment element may include adjusting a flow of coolant within the cryoballoon, for example, stopping, reducing, or redirecting the flow of coolant within the cryoballoon. The treatment element may include a coolant injection element and a plurality of ports (which may be defined by the coolant injection element), both the coolant injection element and the plurality of ports being in fluid communication with the coolant supply reservoir. Redirecting the flow of coolant may include modifying the flow of coolant through the plurality of ports. For example, the fluid injection element may be rotatably disposed within the cryoballoon, and rotating the fluid injection element may change the direction of coolant flow. Additionally or alternatively, the fluid injection element may include a shield element that blocks the flow of coolant from one or more ports.

In another embodiment, the system may include a cryoablation device having a treatment element, one or more thermocouples coupled to the treatment element, and a coolant injection element disposed within the treatment element, a coolant supply reservoir in fluid communication with the treatment element, and a control unit in communication with the one or more thermocouples, the control unit including a processor programmable to receive temperature measurements from the one or more thermocouples and to calculate a slope of temperature change over time, the control unit adjusting the flow of coolant within the treatment element in response to a change in the rate of change in temperature detected by the processor. For example, the control unit may adjust the flow of coolant within the treatment element when the processor detects an increase in the rate of change in temperature. Alternatively, the control unit may adjust the flow of coolant within the treatment element at a predetermined time from the time at which the processor detects an increase in the rate of change in temperature. The coolant injection element may define a plurality of ports, which may be in fluid communication with the coolant supply reservoir. Adjusting the flow of coolant may include modifying the flow of coolant through the plurality of ports and/or it may include redirecting the flow of coolant from the fluid injection element.

In another embodiment, a system for cryoablation lesion depth assessment in myocardial tissue may include a cryoablation device having a balloon at a distal end of the cryoablation device, a plurality of thermocouples disposed on the balloon, and a fluid injection element disposed within the balloon, the coolant injection element including a plurality of fluid ports. The system may further include a fluid supply reservoir in fluid communication with the plurality of fluid ports and a control unit in communication with the one or more thermocouples and with the fluid injection element, the control unit including a processor programmable to receive temperature measurements from the one or more thermocouples and to calculate a rate of change in temperature, the control unit adjusting the flow of fluid from the fluid injection element in response to a change in the rate of change in temperature detected by the processor. For example, adjusting the flow of fluid from the fluid injection element may include redirecting the flow of fluid from the plurality of fluid ports away from one or more thermocouples that detect an increased rate of change in temperature. The control unit may adjust the flow of fluid from the plurality of fluid ports when the processor detects an increase in the rate of change in temperature or at a predetermined time thereafter.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
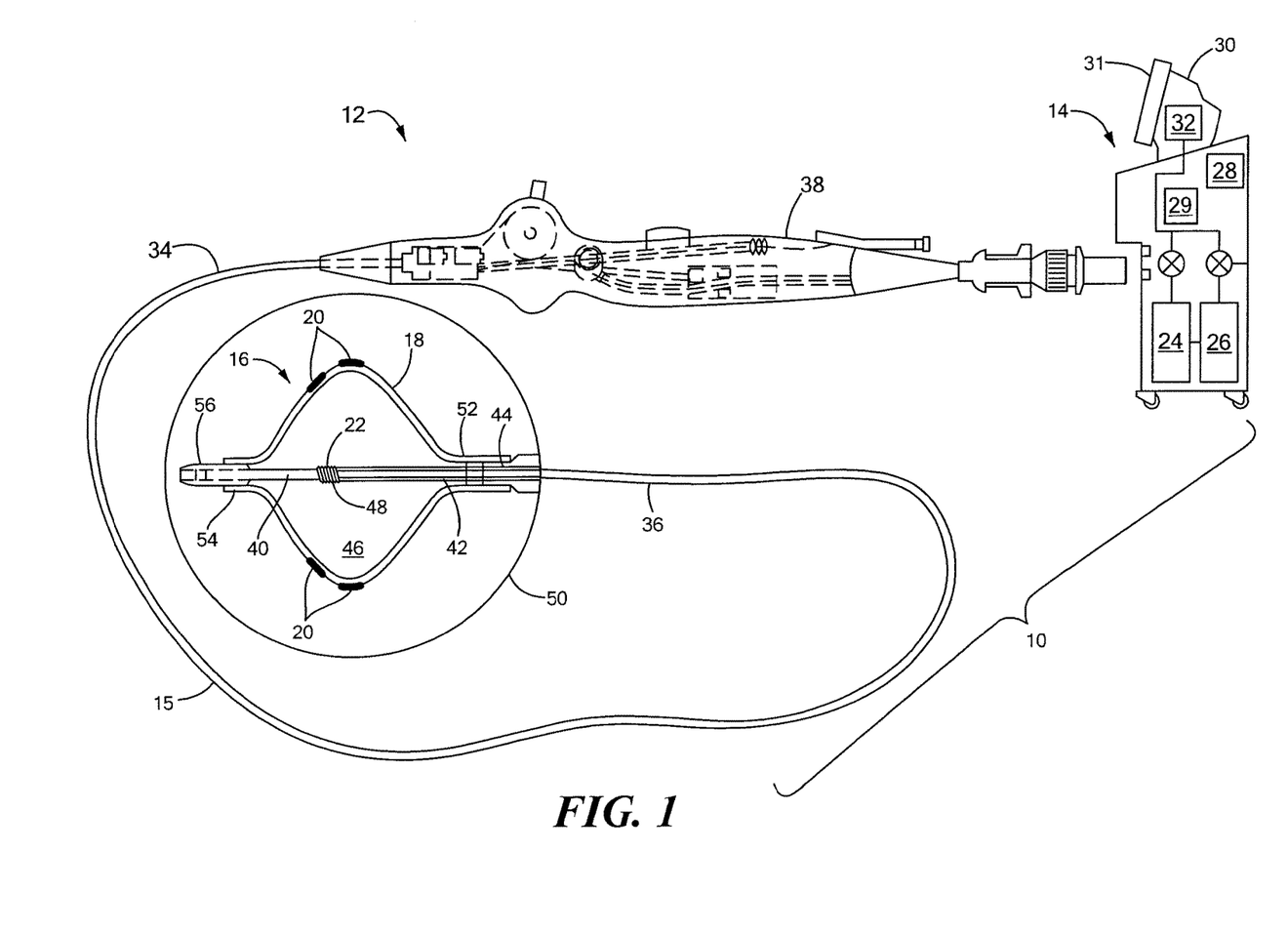
FIG. 1 shows an exemplary ablation system having a first embodiment of a cryoablation device in accordance with the present invention.

Referring now to the drawing figures in which like reference designations refer to like elements, an embodiment of a medical cryoablation system constructed in accordance with the principles of the present invention is shown in FIG. 1 and generally designated as "10." The system 10 generally includes a medical device 12 that may be coupled to a control unit 14 or operating console. The medical device 12, for example, a cryoablation device as shown in the figures, may generally include an elongate body 15 and one or more diagnostic or treatment elements 16 for energetic, therapeutic and/or investigatory interaction between the medical device 12 and a treatment site. For example, the treatment element 16 may include a balloon 18, one or more temperature sensors 20, and a coolant injection element 22. The treatment element 16 may deliver, for example, cryogenic therapy to a tissue area in proximity to a treatment region, including cardiac tissue and/or pulmonary vein tissue. It will be understood that the ablative energy source can also be a fluid or gas at a high temperature, in addition to or instead of a cryogenic agent. For example, they system 10 may be used to apply energy to tissue, such as radiofrequency energy, ultrasound energy, laser energy, microwave energy, or the like.

The control unit 14 may include a coolant supply reservoir 24 including one or more reservoirs for one or more coolants, cryogenic refrigerants, or the like, an exhaust or scavenging system for recovering or venting expended fluid for reuse or disposal (including, for example, a coolant recovery reservoir 26 and pump 28), as well as various control mechanisms. In addition to providing an exhaust function for the coolant supply, the control unit 14 may also include pumps 28, valves, controllers or the like to recover and/or re-circulate fluid delivered to various fluid pathways of the system 10 and/or medical device 12. For example, a vacuum pump 28 in the control unit 14 may create a low-pressure environment in one or more conduits within the medical device 12 so that fluid is drawn into the conduits/lumens of the elongate body 15, away from the treatment element 16. The control unit 14 may be in communication with the one or more temperature sensors 20 and the coolant injection element 22.

In addition to or instead of the coolant supply reservoir 24, the control unit 14 may also include an energy generator 29 that is in electrical communication with one or more electrodes on the treatment element 16. Thus, the system may be used to additionally or alternatively deliver thermal energy to ablate tissue.

The control unit 14 may also include one or more components for the manual and/or automatic regulation of the system, such as a computer 30 having one or more displays 31 and one or more processors 32 for executing one or more algorithms for the automatic regulation of the device 12 before, during, and after an ablation procedure. For example, the processor 32 may be programmable to inflate and deflate one or more cryoballoons of the treatment element (such as according to a user-programmed duty cycle or an automated duty cycle), to regulate temperature of the treatment element, to adjust the flow of coolant from the coolant injection element 22, and/or to receive and interpret mapping or sensor signals from the cryoablation device 12 or another device used as part of a medical procedure. Although various system components may be shown and described herein as being within the control unit 14, the term "control unit" as used herein refers to any system component other than the cryoablation device 12 and other devices that are passed into the patient to perform the medical procedure, regardless of whether the components are physically located within the control unit 14.

Continuing to refer to FIG. 1, the medical device 12 may include an elongate body 15 passable through a patient's vasculature and/or proximate to a tissue region for diagnosis or treatment, such as a catheter, sheath, or intravascular introducer. Accordingly, the elongate body 15 may be composed of a biocompatible material that is sufficiently flexible to safely pass through tortuous pathways of the patient's vasculature. The elongate body 15 may define a proximal portion 34 and a distal portion 36, and may further include one or more lumens or conduits disposed within the elongate body 15 thereby providing mechanical, electrical, and/or fluid communication between the proximal portion 34 of the elongate body 15 and the distal portion 36 of the elongate body 15. The proximal portion 34 of the elongate body 15 may include a handle 38 having one or more knobs, levers, connectors, umbilicals, and other components used for steering, manipulating, and operating the device 12 and connecting the device 12 to the control unit 14.

The medical device 12 may further include an elongate guide wire lumen 40 at least partially disposed within a portion of the elongate body 15. The guide wire lumen 40 may extend or otherwise protrude from a distal end of the elongate body 15, and may be movable with respect to the elongate body 15 in longitudinal and rotational directions. That is, the guide wire lumen 40 may be slidably and/or rotatably moveable with respect to the elongate body 15. Alternatively, the guide wire lumen 40 may be affixed or coupled to the elongate body 15 such that the guide wire lumen 40 has a fixed position and is not slidably and/or rotatably moveable with respect to the elongate body 15. Further, the guide wire lumen 40 may be as flexible, more flexible, or less flexible than the elongate body 15. For example, if it is desirable to provide a device with a distal portion that is more easily steerable or bendable than the elongate body, then the guide wire lumen 40 may be more flexible (that is, be composed of a material having a lower flexural modulus) than the elongate body 15. Conversely, if a more rigid distal portion is desired, the guide wire lumen 40 may be less flexible or more rigid (that is, be composed of a material having a higher flexural modulus) than the elongate body 15.

The guide wire lumen 40 may include or define a coolant delivery conduit 42 that is in fluid communication with the coolant supply reservoir 24 to deliver coolant from the proximal portion 34 of the elongate body 15 and/or the control unit 14 to the distal portion 36 of the elongate body 15 and/or treatment region 16 of the device 12. The guide wire lumen 40 may also include or define coolant recovery conduit 44 that is in fluid communication with the scavenging system. Further, the device 12 may include a coolant injection element 22 that is disposed within the expansion chamber 46 of the balloon 18. The coolant injection element 22 may have any of a variety of configurations, such as those shown in the non-limiting embodiments of FIGS. 1-6. In the first device embodiment shown in FIG. 1, the coolant injection element 22 may be a distal portion of the coolant delivery conduit 42 and may be wound about the guide wire lumen 40 in one or more coils. The coolant injection element 22 may define one or more ports 48 for expelling coolant into the expansion chamber 46 of the balloon 18. Further, the coolant may be expelled radially from the one or more ports 48 toward an inner surface of the balloon 18.

The treatment element 16 may be located at a distal end 50 of the device 12. As shown in FIG. 1, for example, the treatment element 16 may include a cryoballoon 18. In a non-limiting embodiment, the balloon 18 may include a proximal neck 52 and a distal neck 54. The proximal neck 52 may be coupled to (for example, adhered with a biocompatible adhesive or bonded to) the distal portion 36 of the elongate body 15, and the distal neck 54 may be coupled to (as is the proximal neck 52) the distal portion 56 of the guide wire lumen 40. However, it will be understood that the balloon 18 may be coupled to the distal end 50 of the device 12 in any manner that allows for inflation of the balloon without leaking coolant into the patient's body. Further, although not shown, the treatment element 16 may include a second balloon disposed on the outside or inside of the first balloon 18 to offer additional protection against leaks and tears. Additionally, the balloon 18 (or the outer balloon when more than one balloon are used) may further include one or more layers providing for puncture resistance, radiopacity, or the like, and may also be substantially electrically insulative.

The one or more temperature sensors 20 may be any type of temperature sensor, for example, thermocouples or thermistors, even though referred to herein as thermocouples. The one or more thermocouples 20 may be disposed on an outer surface or expansion surface of the balloon 18, such that one or more thermocouples 20 are in contact with the target tissue. For example, one or more thermocouples 20 may be integrated with or coupled to or otherwise affixed to an outer surface of the balloon 18. The one or more thermocouples 20 may be in electrical communication with the control unit 14 to transmit temperature measurement signals from the treatment element 16 to the control unit 14 (for example, a computer 30). Further, the thermocouples 20 may be capable of transmitting signals to the control unit 14 relating to impedance measurements from the tissue with which they are in contact. This may allow a user to use the impedance signals from the one or more thermocouples 20 to monitor the contact between the one or more thermocouples and tissue. The user may disregard temperature measurements from thermocouples 20 whose impedance values indicate a lack of good contact with tissue. Additionally or alternatively, the one or more processors 32 may be programmable to automatically disregard temperature measurements from such thermocouples 20 and/or to generate an alert (for example, an audio alert and/or a visual alert shown on a display 31) to notify the user of the insufficient tissue contact. As a non-limiting example, the one or more thermocouples 20 may be T-type (copper-constantan) thermocouples, which are biocompatible, non-magnetic, and generally recognized as being some of the most accurate thermocouples.

Figure 2A:
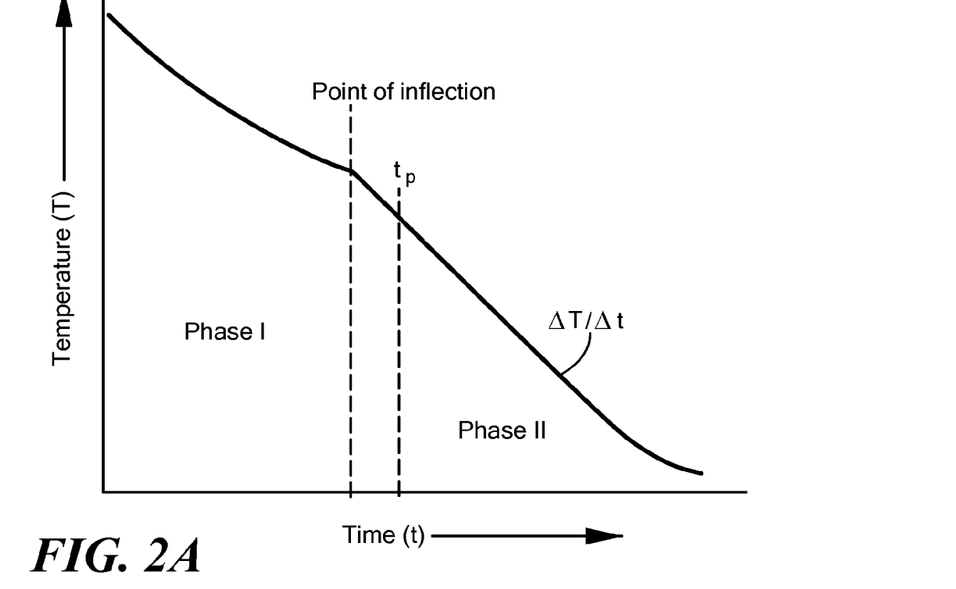
FIG. 2A shows a chart showing a change in temperature over time as cryoablation temperatures reach non-myocardial tissue.
Figure 2B:
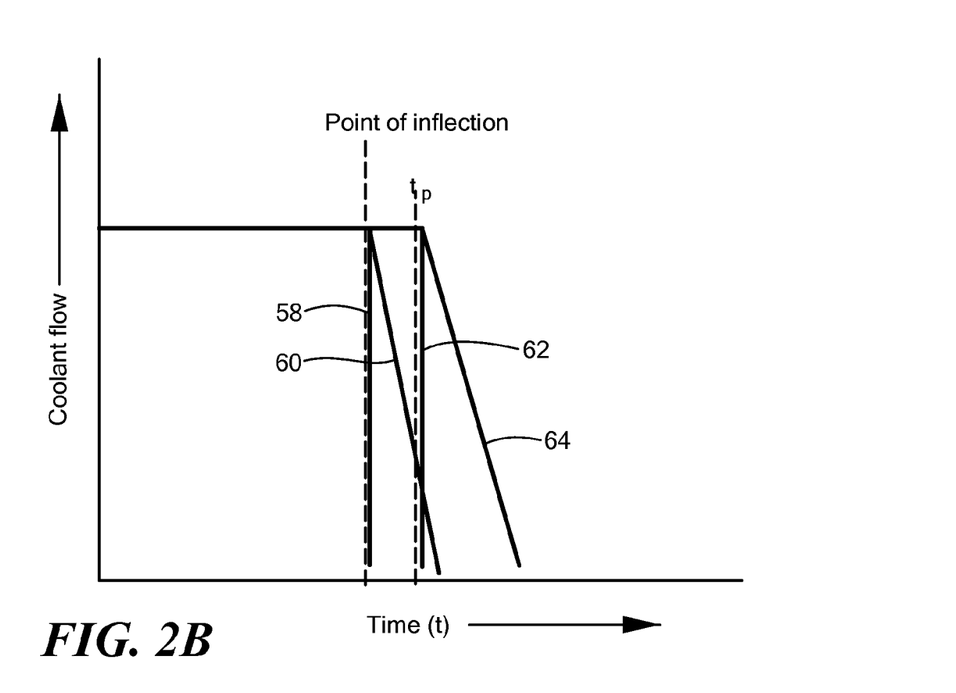
FIG. 2B shows a chart showing coolant flow within a treatment element over time.

Referring now to FIGS. 2A and 2B, a chart showing a change in temperature over time as cryoablation temperatures reach non-myocardial tissue and a chart showing the flow of coolant over time are shown. The temperature measurement signals from the one or more thermocouples 20 may be used by the one or more processors 32 to determine a rate of change in temperature ($\Delta T$) for each thermocouple 20 over time (t). For example, the one or more processors 32 may include a timing circuit for measuring a time duration over which temperature is measured. The slope $\Delta T/\Delta t$ may be viewed as the change in the residual latent heat of solidification. As the latent heat capacity of the surrounding bio-material (for example, lung tissue) is much smaller than that of myocardial tissue, the ice freezing interface is therefore accelerating once the myocardial tissue is frozen transmurally. As the thermal conductivity of frozen tissue is higher than non-frozen tissue, this also contributes to acceleration of the drop in temperature ($\Delta T/\Delta t$ is increasing in the negative side) in the myocardial tissue. As shown in FIG. 2A, the cryoablation temperature isotherm, or "freezing interface," may accelerate once it reaches non-myocardial tissue. In other words, the thermal gradient (or slope $\Delta T/\Delta t$) may be monitored to determine when the freezing interface has moved through the target myocardial tissue and into non-target tissue. Using this thermal phenomenon, the flow of coolant through the balloon 18, or thermal energy transmitted from the energy generator 29 to one or more electrodes, may be adjusted to prevent thermal damage to non-target tissue, such as that of the lungs, phrenic or vagus nerve, esophagus, or other non-myocardial tissues proximate the treatment site.

In a cryoablation system, during Phase I, the change in temperature ΔT of the target myocardial tissue may decrease over time t as the balloon 18 removes an increasing amount of heat from the tissue. That is, the slope ΔT/Δt may have a negative value during the period of time during which target myocardial tissue is the only tissue being thermally affected by the balloon 18. During Phase II, the change in temperature ΔT of the target myocardial tissue may continue to decrease over time t; however, the slope ΔT/Δt may have a more negative value than that during Phase I, as shown in FIG. 2A (that is, the slope value may increase negatively). This relates to the phenomenon wherein the freezing interface may accelerate faster in non-myocardial tissue, and the change in thermal gradient may indicate the point at which the circulation of coolant within the balloon 18 may be modified to prevent collateral damage to non-myocardial tissue. The point between Phases I and II may be referred to as the "point of inflection." In a similar manner, the slope ΔT/Δt may have a less negative value than that during Phase I, also indicating a transition through a different type of non-myocardial tissue. For example, an increase in the rate of change (that is, a more negative value of slope ΔT/Δt than in Phase I) may indicate that the freezing interface has moved from myocardial tissue to tissue that is more thermally conductive than myocardial tissue. On the other hand, for example, a decrease in the rate of change (that is a more positive value of slope ΔT/Δt than in Phase I) may indicate that the freezing interface has moved from myocardial tissue to tissue that is less thermally conductive than myocardial tissue. Still further, the type of non-myocardial tissue the freezing interface has come into contact with may be determined based on the value of slope ΔT/Δt. For example, even though two tissue slope values may be more negative than in Phase I, they may be different from each other. That is, of two tissue types that are more thermally conductive than myocardial tissue, one may be more thermally conductive than the other. Accordingly, this comparison may be used to differentiate between several tissue types.

As shown in FIG. 2B, coolant may be circulated at a steady flow rate during Phase I. Once the change in thermal gradient (or slope ΔT/Δt) indicates the freezing interface has moved into non-myocardial tissue (either that non-myocardial tissue that is more or less thermally conductive than myocardial tissue), the flow of coolant may be adjusted in any of several ways. For example, the flow of coolant may be immediately stopped at the point of inflection (as represented in FIG. 2B by flow line 58) or the flow of coolant may be reduced or redirected at the point of inflection (as represented in FIG. 2B by flow line 60). Alternatively, the flow of coolant may be stopped at a predetermined time $t_p$ after the point of inflection is reached (as represented in FIG. 2B by flow line 62) or the flow of coolant may be reduced or redirected at a predetermined time $t_p$ after the point of inflection is reached (as represented in FIG. 2B by flow line 64) as the inflection point may indicate the point at which the tissue is frozen transmurally, which may be different than the lethal temperature of the tissue.

In thermal ablation system, the slope ΔT/Δt may positively increase at the inflection point, as the temperature of non-myocardial tissue will increase more rapidly than that of myocardial tissue in Phase I. Once the change in thermal gradient (or slope ΔT/Δt) indicates the "heating interface" has moved into non-myocardial tissue (either that non-myocardial tissue that is more or less thermally conductive than myocardial tissue), the amount of energy transmitted to and delivered by the treatment element 16 may be adjusted in any of several ways. For example, the energy delivery may be immediately stopped at the point of inflection or the energy delivery may be reduced or redirected at the point of inflection. Alternatively, the energy delivery may be stopped at a predetermined time $t_p$ after the point of inflection is reached or the energy delivery may be reduced or redirected at a predetermined time $t_p$ after the point of inflection is reached, as the inflection point may indicate the point at which the tissue is heat ablated transmurally, which may be different than the lethal temperature of the tissue.

Thermal gradient may be monitored for each thermocouple 20 individually, which may allow the user and/or the control unit 14 to determine the location relative to the balloon 18 of the non-target tissue that may be in danger of suffering collateral damage. Additionally, it may allow the user and/or the control unit 14 to pay particular attention to signals from one or more thermocouples 20 that are closest to non-target structures that are likely to be thermally affected by the treatment. For example, one or more thermocouples 20 nearest the esophagus may be given priority. Additionally, signals from the one or more thermocouples 20 may be evaluated collectively or in subsets to assess the local and/or regional impact of the cryoablation procedure on adjacent tissues and to provide redundancy when making decisions regarding the modulation or adjustment of coolant circulation through the balloon 18.

The flow of coolant through the system 10, including the balloon 18, may be stopped or reduced manually by the user and/or automatically by the control unit 14 when one or more thermocouples 20 indicate that the freezing interface has reached non-myocardial tissue (that is, that the point of inflection has been reached). This adjustment may be accomplished, for example, by the manual and/or automatic opening or closing of one or more valves throughout the system 10. For example, in the cryoablation device embodiment shown in FIG. 1, redirection of coolant flow may not be feasible, so coolant flow may be stopped or reduced. Further, the treatment element 16 may include one or more means for redirecting the flow of coolant away from thermocouples 20 that indicate the point of inflection has been reached. Redirection of coolant flow away from these thermocouples 20 may increase the local temperature in those areas of the balloon 18, thereby reducing the thermal impact on non-myocardial tissues corresponding to those areas. Non-limiting examples of means for redirecting coolant flow are shown and described in more detail in FIGS. 3A-7.

Figure 3A:
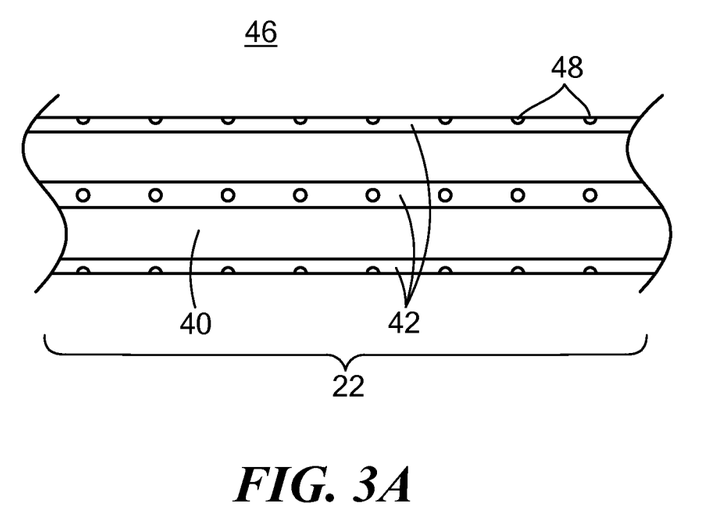
FIG. 3A shows a second exemplary cryoablation device in accordance with the present invention.
Figure 3B:
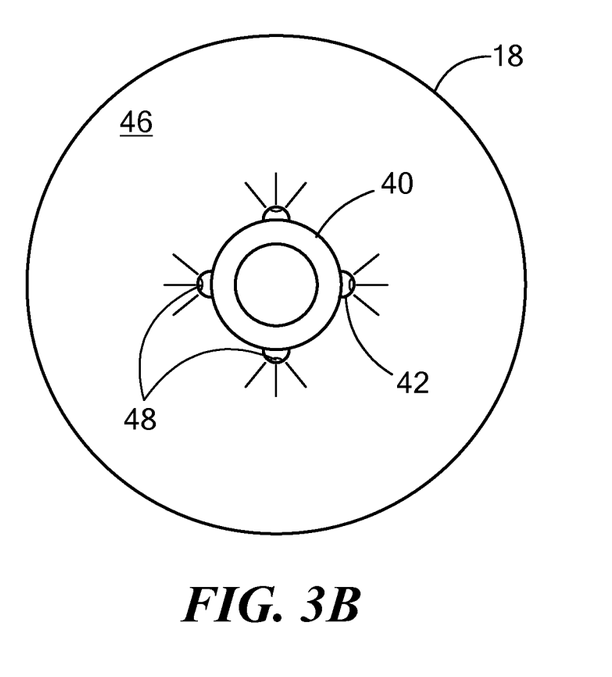
FIG. 3B shows a cross-sectional view of a guide wire lumen of the device of FIG. 3A.

Referring now to FIGS. 3A and 3B, a second exemplary cryoablation device in accordance with the present invention is shown. The coolant injection element 22 may include a plurality of coolant delivery conduits 42, each in fluid communication with the coolant supply reservoir 24, that are coupled to or otherwise affixed to an outer surface of the guide wire lumen 40. Each coolant delivery conduit 42 may define one or more ports 48, which may be radially oriented about the longitudinal axis of the guide wire lumen 40. The coolant flow may be redirected by stopping or reducing coolant flow independently to one or more fluid delivery conduits 42 that spray coolant in the direction of the non-target tissue implicated by the temperature measurements by one or more thermocouples 20.

Figure 4A:
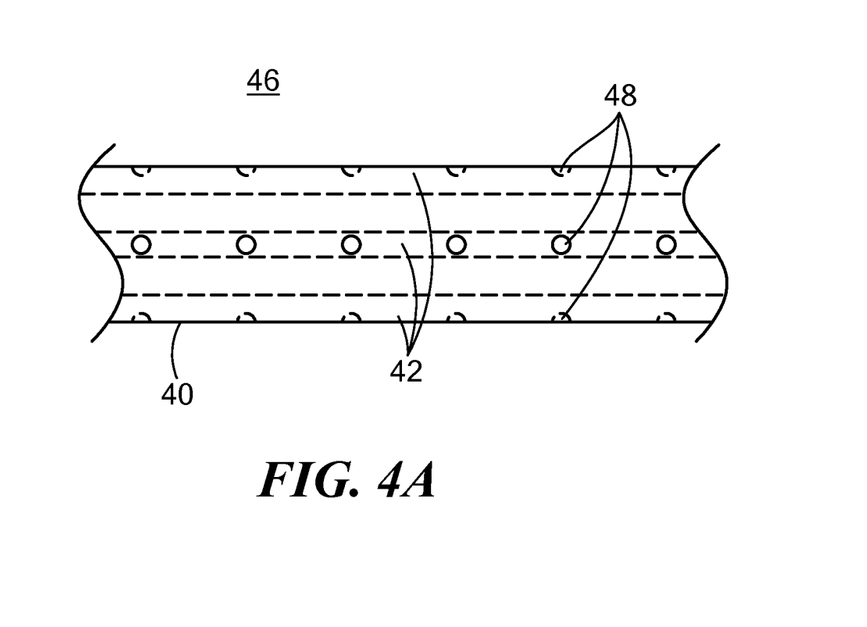
FIG. 4A shows a third exemplary cryoablation device in accordance with the present invention.
Figure 4B:
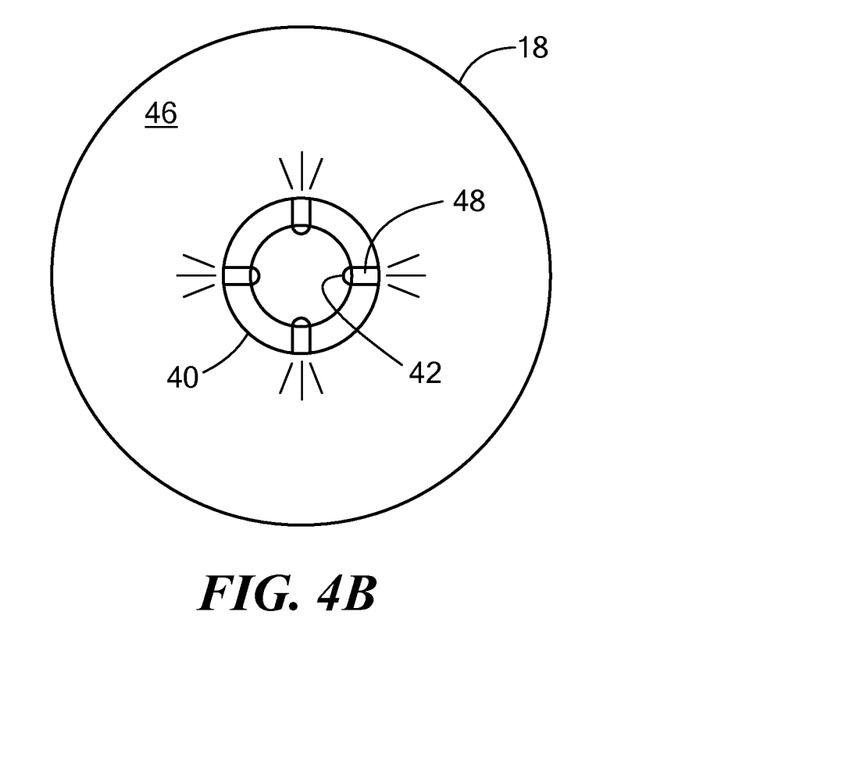
FIG. 4B shows a cross-sectional view of a guide wire lumen of the device of FIG. 4A.

Referring now to FIGS. 4A and 4B, a third exemplary cryoablation device in accordance with the present invention is shown. The third embodiment may be largely the same as the second embodiment, except that the coolant injection element 22 may be integrated with the guide wire lumen 40, with the plurality of coolant delivery conduits 42 being disposed within the guide wire lumen 40 and the guide wire lumen 40 defining one or more ports 48. In this embodiment, the guide wire lumen 40 may be included as a component of the fluid injection element 22. The coolant flow may be redirected as described in FIGS. 3A and 3B.

Figure 5A:
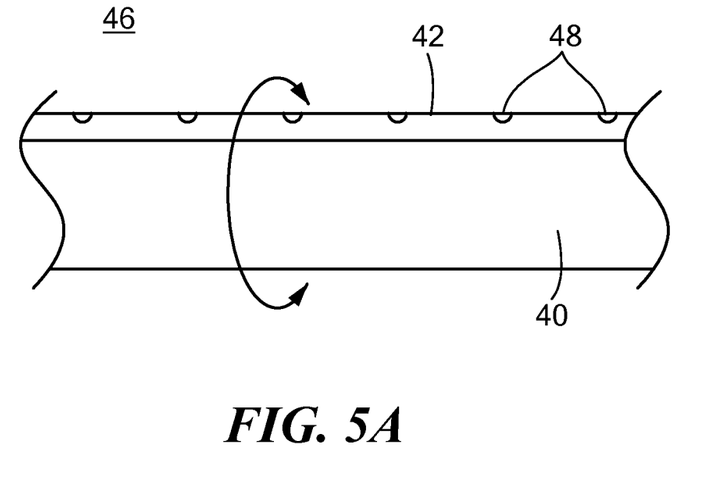
FIG. 5A shows a fourth exemplary cryoablation device in accordance with the present invention.
Figure 5B:
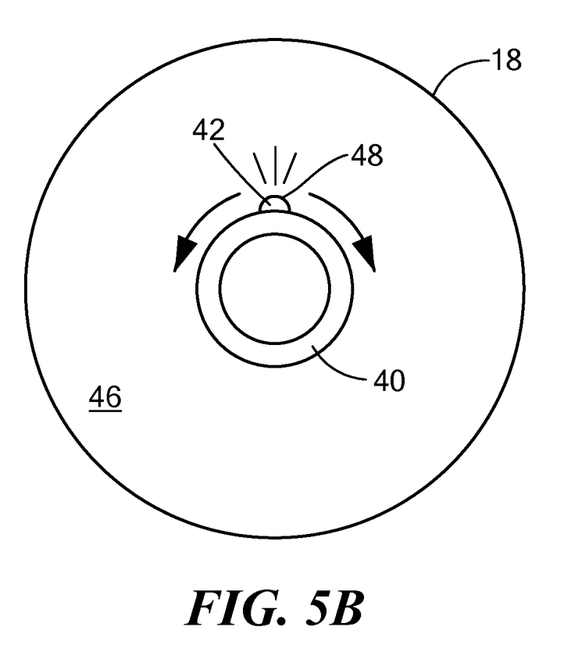
FIG. 5B shows a cross-sectional view of a guide wire lumen of the device of FIG. 5A.

Referring now to FIGS. 5A and 5B, a fourth exemplary cryoablation device in accordance with the present invention is shown. In this embodiment in particular, the guide wire lumen 40 may be rotatably disposed within the elongate body 15. The coolant injection element 22 may include a single coolant delivery conduit 42 that is either coupled to an outer surface of the guide wire lumen (as shown in FIG. 3A) or disposed within the guide wire lumen 40 (as shown in FIGS. 4A and 5A). If the coolant delivery conduit 42 is coupled to an outer surface of the guide wire lumen 40, the coolant delivery conduit 42 may define a plurality of ports 48. Alternatively, if the coolant delivery conduit 42 is disposed within the guide wire lumen 40, the guide wire lumen may define a plurality of ports 48. The coolant flow may be redirected by rotating the guide wire lumen 40 to reposition the ports 48, thereby spraying coolant away from the direction of the non-target tissue implicated by the temperature measurements by one or more thermocouples 20. The guide wire lumen 40 may be rotated manually by the user, automatically by the system, or a combination thereof. As a non-limiting example, automatic rotation may be accomplished using a stepper motor in the handle of the device.

Figure 6A:
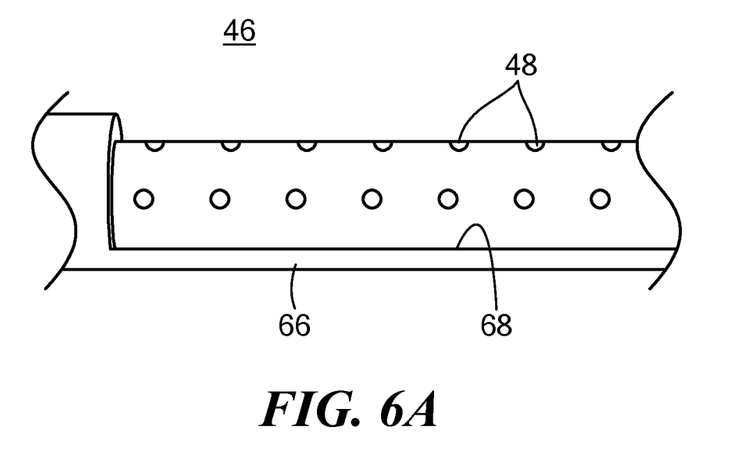
FIG. 6A shows a fifth exemplary cryoablation device in accordance with the present invention.
Figure 6B:
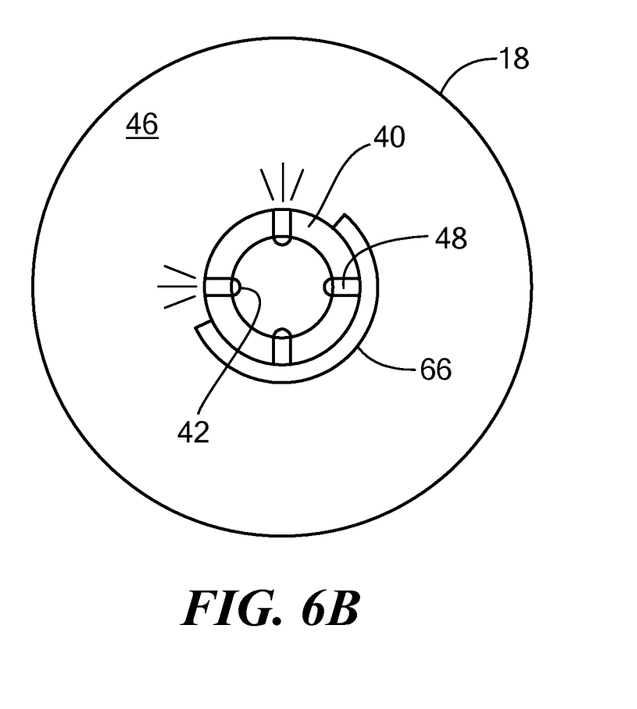
FIG. 6B shows a cross-sectional view of a guide wire lumen of the device of FIG. 6A.

Referring now to FIGS. 6A and 6B, a fifth exemplary cryoablation device in accordance with the present invention is shown. The coolant ejection element 22 may include a plurality of ports 48 defined by the guide wire lumen 40 and a spray shield 66 rotatably disposed about at least a portion of the guide wire lumen 40. The spray shield 66 may define an opening 68 that is large enough to expose one or more ports 48. As a non-limiting example, the shield 66 shown in FIG. 6A may include an opening 68 that is large enough to expose two rows of ports 48. The coolant flow may be redirected by rotating the shield 66 relative to the guide wire lumen 40 to expose or cover one or more ports 48.

Figure 7:
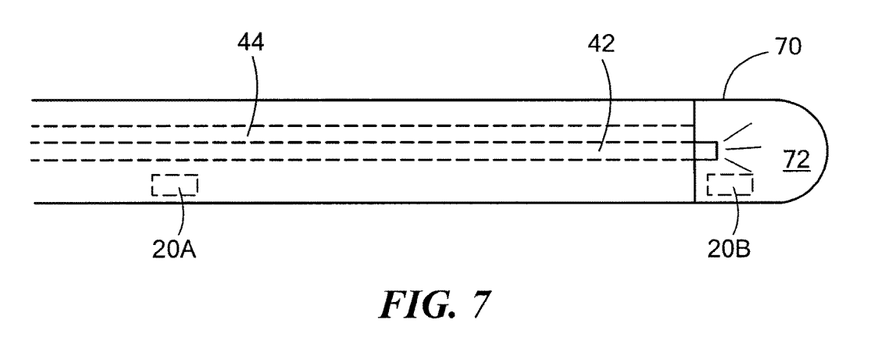
FIG. 7 shows a sixth exemplary cryoablation device in accordance with the present invention.

Referring now to FIG. 7, a sixth exemplary cryoablation device in accordance with the present invention is shown. Unlike the embodiments of FIGS. 1-6B, the embodiment shown in FIG. 7 may not include a balloon 18 or other expandable element through which coolant is circulated. Instead, the device 12 may have a continuous diameter, which configuration may be referred to as a focal catheter. The device 12 may include an electrode or area of conductive material 70 that is in thermal communication with a thermoelectric element (not shown) or an expansion chamber 72 through which coolant is circulated. The device may further include a thermocouple 20 integrated with or coupled to or otherwise affixed to an outer surface of the elongate body 15 proximate the area of conductive material 70 (as shown by the non-limiting example of placement of thermocouple 20A in FIG. 7) or affixed to an inner or outer surface of the conductive material 70 (as shown by the non-limiting example of placement of thermocouple 20B in FIG. 7). As in the device shown and described in FIG. 1, the device of FIG. 7 may not include a means for redirecting coolant flow. Instead, the flow of coolant through the expansion chamber 72 may be stopped or reduced manually or automatically. Alternatively, the area of conductive material 70 may extend along at least a portion of the length of the elongate body, and coolant flow may be adjusted and/or selectively directed toward an inner surface of one or more areas of the conductive material 70, similar to what is shown and described in FIGS. 3A-6B. Additionally, it will be understood that the flow of coolant may simply be stopped or reduced at or after the point of inflection, regardless of whether the device 12 includes a means for redirecting the flow of coolant away from non-target tissue. Although not shown in the figures, it will be understood that thermal energy may be redirected by, for example, relocating, deactivating, and/or adjusting the amount of energy delivered by one or more electrodes.

Figure 8:
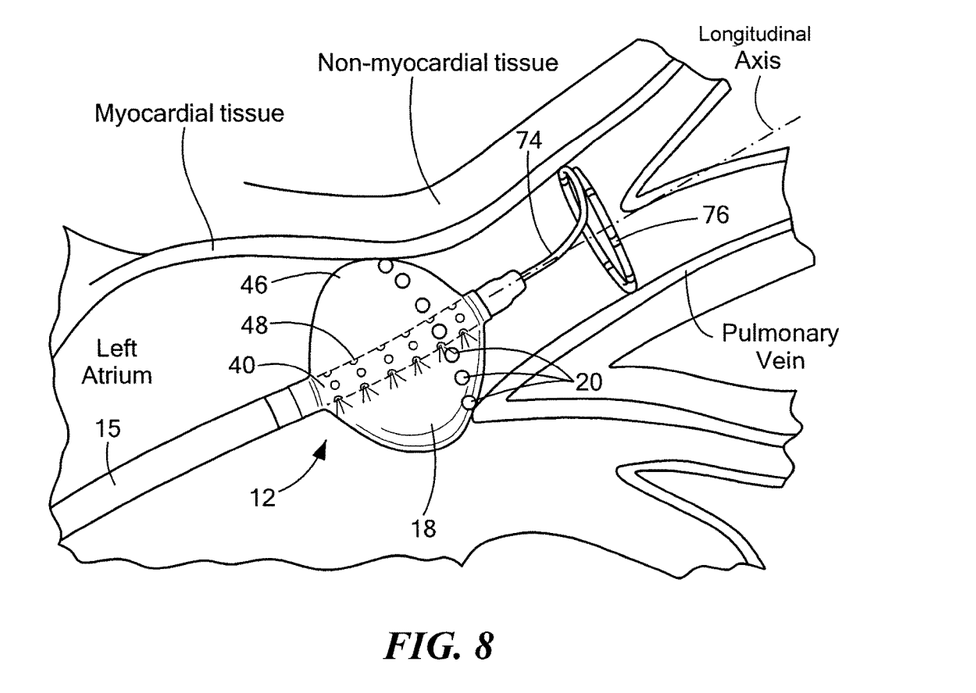
FIG. 8 shows a cryoablation device positioned within a heart in contact with a pulmonary vein ostium.

Referring now to FIG. 8, a cryoablation device positioned within a heart in contact with a pulmonary vein ostium is shown. This is a non-limiting example of how the device 12 may be positioned during a cryoablation procedure, and the device 12 may alternatively be positioned at any location within the heart. As shown in FIG. 8, the balloon 18 may be positioned in contact with a pulmonary vein ostium such that one or more thermocouples 20 are in contact with target myocardial tissue. In this position, signals from the one or more thermocouples 20 may be used to assess tissue contact using impedance measurements and to monitor ablation depth using temperature measurements over time. As shown in FIG. 8, the device 12 may include a mapping catheter passable through the guide wire lumen 40. The mapping catheter 74 may include a plurality of mapping electrodes 76 for mapping, for example, pulmonary vein tissue to confirm whether cryoablation has interrupted aberrant electrical signals originating from within the pulmonary vein. However, the mapping catheter 74 may be used to map other areas of the heart as well.

Figure 9:
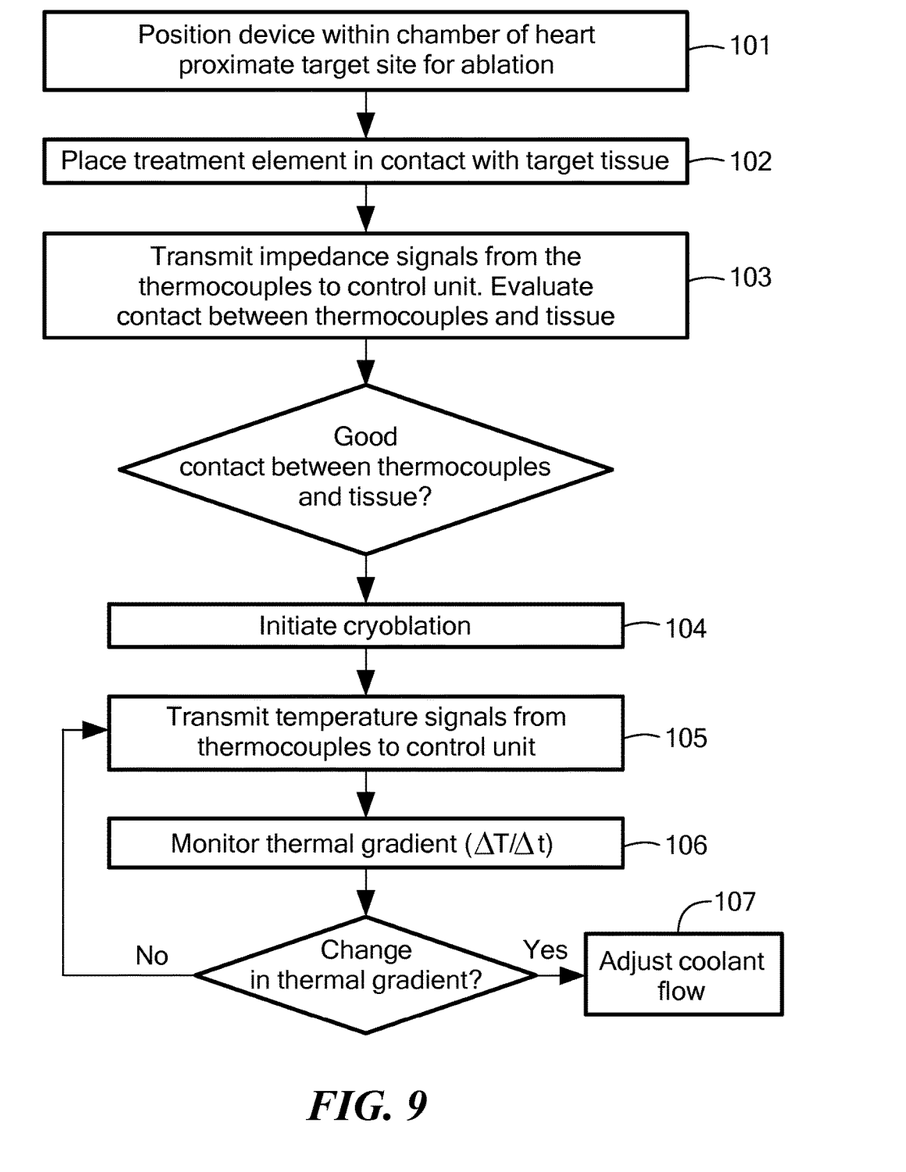
FIG. 9 shows a flowchart for a method of ablating target tissue without damaging non-target tissue.

Referring now to FIG. 9, a flowchart for a method of ablating target tissue without damaging non-target tissue is shown. In the first step 101 of the method, the device may be positioned within a chamber of the heart proximate the target site for ablation. For example, the device may be placed in the left atrium if the target site is a pulmonary vein ostium. In the second step 102 of the method, the treatment element 16 may be placed in contact with target tissue. In embodiments having a balloon 18, the balloon may first be inflated by initiating the flow of coolant into the expansion chamber 46. However, this initial coolant flow may not be at a rate or temperature sufficient to cryoablate tissue. In the third step 103 of the method, impedance signals may be transmitted from the one or more thermocouples 20 to the control unit 14 (for example, to the one or more processors 32) and used to evaluate whether there is good contact between the thermocouple 20 transmitting the signal and the tissue. The device 12 may be repositioned as required until there is good contact between the target tissue and one or more thermocouples 20.

In the fourth step 104 of the method, the flow of coolant at cryogenic temperatures may be initiated. In other words, cryoablation of target tissue may begin. In the fifth step 105 of the method, temperature signals may be transmitted from the one or more thermocouples 20 to the control unit 14 (for example, to the one or more processors 32). As described in FIGS. 2A and 2B, temperature measurements may be evaluated over time, giving a thermal gradient value $\Delta T/\Delta t$. Further, temperature measurements may be assessed from individual thermocouples 20, or they may be assessed collectively or in subsets. Still further, temperature measurements from thermocouples 20 proximate an area of non-target tissue that may be particularly affected by the procedure may be given priority. For example, temperature measurement signals received from thermocouples 20 closest to the esophagus may be given more weight than those received from more distant thermocouples 20.

In the sixth step 106 of the method, the thermal gradient may be monitored during cryoablation. Once the point of inflection is reached (that is, once the slope $\Delta T/\Delta t$, or rate of change in temperature over time, has either increased or decreased), the flow of coolant may be adjusted in the seventh step 107 of the method. As shown and described in FIGS. 1-7, the coolant flow may be stopped, reduced, or redirected. Further, coolant flow may be adjusted at either the point of inflection or at a predetermined time $t_p$ after the point of inflection is reached. As an optional step, other methods (such as ultrasonography, radiography, fluoroscopy, and bioimpedance measurements) may be used to confirm that no collateral damage is caused to non-cardiac tissue. The thermal gradient may have different characteristics depending on the type of tissue the freezing interface passes into from the myocardial tissue.

Although many of the devices, systems, and methods shown and described herein relate to cryoablation, the evaluation of thermal gradient to indicate the freezing interface has passed through target myocardial tissue into non-target tissue may be used for other energy modalities as well, including radiofrequency (RF) ablation, thermal ablation using heated fluids, and ultrasound ablation. In such systems, one or more thermocouples may be located proximate one or more energy delivery electrodes, and the impedance and temperature feedback from the thermocouples may be used by the user and/or the control unit to monitor thermal gradient and the onset of the point of inflection. At the point of inflection or at a predetermined time after the point of inflection is reached, the delivery of energy from the one or more electrodes may be adjusted. For example, the energy delivery may be stopped or reduced. Further, each electrode may be controlled independently It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for ablation lesion depth assessment in myocardial tissue, the system comprising:
a cryoablation device including:
a treatment element;
one or more thermocouples coupled to the treatment element; and
a coolant injection element disposed within the treatment element;
at least one of a coolant supply reservoir in fluid communication with the treatment element and an energy generator in electrical communication with the treatment element;
a control unit in communication with the one or more thermocouples, the control unit including a processor programmed to receive temperature measurements from the one or more thermocouples, to calculate a rate of change in temperature, and to define a point of inflection in the rate of change in temperature at which the calculated rate of change in temperature one of increases and decreases; and
a timing circuit in communication with the control unit for measuring a time duration over which temperature is measured by the one or more thermocouples, the control unit being further programmed to at least one of adjust the flow of coolant within in the treatment element and adjust energy transmitted from the energy generator to the treatment element based on the defined point of inflection.

2. The system of claim 1, wherein the system includes the coolant supply reservoir, the control unit being programmed to adjust the flow of coolant within the treatment element when the processor determines the calculated rate of change in temperature reaches the defined point of inflection.

3. The system of claim 1, wherein the system includes the energy generator, the control unit being programmed to adjust the amount of energy transmitted to the treatment element when the processor determines the calculated rate of change in temperature reaches the defined point of inflection.

4. The system of claim 1, wherein the system includes the coolant supply reservoir, the control unit being programmed to adjust the flow of coolant within the treatment element at a predetermined time from the time at which the processor determines the calculated rate of change in temperature reaches the defined point of inflection.

5. The system of claim 1, wherein the system includes the energy generator, the control unit being programmed to adjust the amount of energy transmitted to the treatment element at a predetermined time from the time at which the processor determines the calculated rate of change in temperature reaches the defined point of inflection.

6. The system of claim 2 wherein the coolant injection element defines a plurality of ports, the plurality of ports being in fluid communication with the coolant supply reservoir.

7. The system of claim 6, wherein the control unit is programmed to adjust the flow of coolant by modifying the flow of coolant through the plurality of ports.

8. The system of claim 6, wherein the control unit is programmed to adjust the flow of coolant by redirecting the flow of coolant from the fluid injection element.

9. The system of claim 2, wherein the cryoablation device further includes a guide wire lumen at least partially disposed within the treatment element and defining a longitudinal axis.

10. The system of claim 9, wherein the coolant injection element defines a plurality of coolant delivery conduits, each of the plurality of coolant delivery conduits including a plurality of ports in flow communication with the coolant supply reservoir.

11. The system of claim 10, wherein each of the plurality of coolant delivery conduits is coupled to the guide wire lumen.

12. The system of claim 11, wherein the plurality of coolant delivery conduits is radially oriented about the longitudinal axis of the guide wire lumen.

13. The system of claim 10, wherein the control unit is programmed to adjust the flow of fluid from the fluid injection element by modifying the flow of coolant through the plurality of ports of the plurality of coolant delivery conduits.

14. The system of claim 13, wherein the control unit is programmed to modify the flow of coolant by one of reducing and stopping the flow of coolant to one or more of the plurality of coolant delivery conduits.

* * * * *